US010010571B2

(12) United States Patent
Durkee et al.

(10) Patent No.: US 10,010,571 B2
(45) Date of Patent: Jul. 3, 2018

(54) NUTRITIONAL SUPPLEMENT FOR THE ENHANCEMENT OF MUSCLE IRISIN AND ENHANCEMENT OF BROWN FAT, METABOLIC RATE, AND WEIGHT LOSS, AND METHODS OF USE THEREOF

(71) Applicant: Maximum Human Performance, LLC, West Caldwell, NJ (US)

(72) Inventors: Shane E. Durkee, Sparta, NJ (US); Gabriel Wilson, Cedar Grove, NJ (US)

(73) Assignee: Maximum Human Performance, LLC, West Caldwell, NJ (US)

( * ) Notice: Subject to any disclaimer, the term of this patent is extended or adjusted under 35 U.S.C. 154(b) by 0 days.

(21) Appl. No.: 15/363,931

(22) Filed: Nov. 29, 2016

(65) Prior Publication Data

US 2017/0151300 A1     Jun. 1, 2017

Related U.S. Application Data

(60) Provisional application No. 62/260,763, filed on Nov. 30, 2015.

(51) Int. Cl.
*A61K 36/424* (2006.01)
*A61K 36/704* (2006.01)
*A23L 33/105* (2016.01)

(52) U.S. Cl.
CPC .......... *A61K 36/424* (2013.01); *A23L 33/105* (2016.08); *A61K 36/704* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 7,867,526 B2 * | 1/2011 | Astrup | A61K 31/198 424/729 |
| 8,029,830 B2 * | 10/2011 | Foley | A61K 31/352 424/702 |
| 8,357,786 B2 | 1/2013 | Huh et al. | |
| 2013/0231492 A1 | 9/2013 | Duan et al. | |

FOREIGN PATENT DOCUMENTS

| CN | 1413706 A | * | 4/2003 |
|---|---|---|---|
| CN | 103609767 A | * | 3/2014 |

OTHER PUBLICATIONS

Arichi, H., et al., Effects of stilbene components of the roots of Polygonum cuspidatum Sieb. et Zucc. on lipid metabolism. Chem Pharm Bull (Tokyo). May 1982;30(5):1766-70.

Baur, JA, et al., Therapeutic potential of resveratrol: the in vivo evidence. Nat Rev Drug Discov. Jun. 2006;5 (6):493-506. Abstract Only.

Bostrom, P., et al., A PGC1α-dependent myokine that drives browning of white fat and thermogenesis. Nature. 481 (7382):463-468, 2012.

Dolinsky, V. W., et al., Improvements in skeletal muscle strength and cardiac function induced by resveratrol during exercise training contribute to enhanced exercise performance in rats. J Physiol. Jun. 1, 2012;590(11):2783-99.

Elliott, PJ, et al., Sirtuins: novel targets for metabolic disease. Curr Opin Investig Drugs. Apr. 2008;9(4):371-8. Abstract Only.

Gauhar, R., et al., Heat-processed Gynostemma pentaphyllum extract improves obesity in ob/ob mice by activating AMP-activated protein kinase. Biotechnol Lett. Sep. 2012;34(9):1607-16. Abstract only.

Hart, N., et al., Resveratrol enhances exercise training responses in rats selectively bred for high running performance. Food Chem Toxicol. Nov. 2013;61:53-9.

Lagouge, M., et al., Resveratrol Improves Mitochondrial Function and Protects against Metabolic Disease by Activating SIRT1 and PGC-1a. Cell. Dec. 15, 2006;127(6):1109-22.

Megalli, S., et al., Anti-Hyperlipidemic and Hypoglycemic Effects of Gynostemma pentaphyllum in the Zucker Fatty Rat. J Pharm Pharm Sci. 2006:9(3):281-91.

Menzies, K. J., et al., Sirtuin 1-mediated Effects of Exercise and Resveratrol on Mitochondrial Biogenesis. J Biol Chem. Mar. 8, 2013:288(10):6968-79.

Murase, T., et al., Suppression of the aging-associated decline in physical performance by a combination of resveratrol intake and habitual exercise in senescence-accelerated mice. Biogerontology. Aug. 2009;10(4):423-34. Abstract Only.

Nguyen, PH, et al., New dammarane-type glucosides as potential activators of AMP-activated protein kinase (AMPK) from Gynostemma pentaphyllum. Bioorg Med Chem. Nov. 1, 2011;19(21):6254-60. Abstract Only.

Park, S., et al., Antiobesity Effect of Gynostemma pentaphyllum Extract (Actiponin): A Randomized, Double-Blind, Placebo-Controlled Trial. Obesity (Silver Spring). Jan. 2014;22(1):63-71.

Price, N. L., et al., SIRT1 is required for AMPK activation and the beneficial effects of resveratrol on mitochondrial function. Cell Metab. May 2, 2012; 15(5): 675-690.

Sugita, J., et al., Grains of paradise (*Aframomum melegueta*) extract activates brown adipose tissue and increases whole-body energy expenditure in men. British Journal of Nutrition (2013), 110,733-738.

(Continued)

*Primary Examiner* — Susan Hoffman
(74) *Attorney, Agent, or Firm* — Amin Talati Upadhye LLP; Adam D. Sussman; George M. Carrera, Jr.

(57) ABSTRACT

The present invention includes a method of activating irisin by administering to an individual in need of such treatment a composition comprising irisin-activating ingredients, thus increasing the conversion of white fat to BAT, and consequently, increasing metabolic rate and promoting weight loss. In an embodiment, the composition includes a *Gynostemma pentaphyllum* extract, a *Polygonum cuspidatum* root extract, capsaicinoids, and grains of paradise or constituents thereof. The composition may optionally comprise additional ingredients to activate the increased BAT, thus further increasing metabolic rate and furthering weight loss.

8 Claims, 7 Drawing Sheets

(56) References Cited

OTHER PUBLICATIONS

Jun Sugita et al., Daily Ingestion of Grains of Paradise (*Aframomum melegueta*) Extract Increases Whole-Body Energy Expenditure and Decreases Visceral Fat in Humans, 60 Journal of Nutritional Science and Vitaminology 22 (2014).
Silvie Timmers et al., Calorie restriction-like effects of 30 days of Resveratrol (resVida) supplementation on energy metabolism and metabolic profile in obese humans, 14 Cell Metabolism (2011).

* cited by examiner

NUTRITIONAL SUPPLEMENT FOR THE ENHANCEMENT OF MUSCLE IRISIN AND ENHANCEMENT OF BROWN FAT, METABOLIC RATE, AND WEIGHT LOSS, AND METHODS OF USE THEREOF

This application claims the benefit of U.S. Provisional Application No. 62/260,763, filed on Nov. 30, 2015. The disclosure of this prior application is incorporated herein by reference in its entirety for all purposes.

TECHNICAL FIELD

The present invention relates to enhancing the levels of the muscle protein irisin, thus promoting the conversion of white fat to brown adipose tissue, consequently increasing metabolic rate and weight loss, in the body of a mammal, including a human, through the use of a composition comprising a *Gynostemma pentaphyllum* extract and a *Polygonum cuspidatum* extract, and optionally additional ingredients to activate the brown adipose tissue.

BACKGROUND

Shivering is the most basic method of maintaining core body temperature during cold exposure, but the human body also has a typically dormant, currently untapped metabolic pathway, which preferentially burns fat for fuel, producing heat. This pathway is called non-shivering thermogenesis. The organ that operates this pathway is called brown adipose tissue ("BAT").

To elaborate, when the human brain begins to sense that the body is exposed to cold temperatures, the brain releases signals to activate BAT. When BAT is activated, levels of uncoupling protein 1 ("UCP-1") are increased, which turns on the entire BAT fat-burning system. When UCP-1 levels are increased in BAT, the body begins to burn body fat.

When adipose tissue or cells, also known as fat tissue, take up nutrients, the adipose tissue typically uses them to produce adenosine triphosphate, thus storing energy for later use. However, UCP-1 effectively disables this process, by targeting the stored energy and burning the stored energy as heat, resulting in an increase in metabolism, and ultimately warming the body during cold stress.

Research shows that BAT activity is higher in lean individuals than in overweight individuals, declines as an individual ages, and also decreases with prolonged dieting. Conversely, activation of BAT in animals and humans results in higher metabolic rates, increases in fat burning, and improves insulin sensitivities. There is a significant inverse correlation between obesity and brown fat levels in the body, with brown fat tending to be higher in lean people than in obese people. Furthermore, when people diet (maintain a caloric deficit) for a sustained period of time, there is a decline in BAT and UCP-1 activity. This suggests that brown fat levels in the body can play an important role in body fat regulation. Thus, BAT activity in the body, or the lack thereof, and/or distribution of BAT in the body, may explain why individuals reach diet plateaus or why some people struggle with weight loss more than others.

Since the discovery of BAT, scientists have been seeking ways to activate dormant BAT in humans, with little success. Previous research has demonstrated that capsaicinoids, and grains of paradise, particularly 6-paradol, are potent brown fat activators. These ingredients were clinically shown to increase metabolism through brown fat oxidation. See M. Iwami et al., *Extract of grains of paradise and its active principle 6-paradol trigger thermogenesis of brown adipose tissue in rats*, 161 AUTON NEUROSCI. 63 (2011); J. Sugita et al., *Grains of paradise (Aframomum melgueta) extract activates brown adipose tissue and increases whole-body energy expenditure in men*, 110 BR. J. NUTR. 733 (2013). However, this same research demonstrates that certain individuals do not respond to the grains of paradise treatment and were termed "non-responders." The non-responders were identified to be "BAT negative" people who did not respond because they lacked the necessary amount of brown fat to be activated. Furthermore, there is a significant correlation between obesity and brown fat levels in the body, demonstrating that brown fat levels in the body can play an important role in body fat regulation.

Irisin is the first hormone identified that is specifically secreted from muscle tissue. Scientists are advertising irisin as the next exercise pill. Irisin was discovered in 2012 and named after the Greek messenger "Iris." Research shows that exercise in humans and animals increases this hormone in muscle, and its increase can be detected in the plasma as well as in muscle and adipose tissue. Irisin travels to adipose tissue, where it increases fat burning and metabolism. In particular, irisin causes "browning" of fat, turning inactive white fat into metabolically active BAT. See, e.g., P. Boström, et al., *A PGC1-α-dependent myokine that drives brown-fat-like development of white fat and thermogenesis*, 481 NATURE 463 (2012); Jorge I. Castillo-Quan, *From white to brown fat through the PGC-1-α-dependent myokine irisin: implications for diabetes and obesity*, 5 DISEASE MODELS & MECHANISMS 293 (2012); F. Villarroya, *Irisin, turning up the heat*, 15 CELL METABOLISM 277 (2012); D. P. Kelly, *Irisin, Light My Fire*, 336 SCIENCE 42 (2012); M. Elsen et al., *Browning of white fat: Does irisin play a role in humans?*, 222 J. ENDOCRINOLOGY R25 (2014).

To date, no supplement or food has been shown to demonstrate activation of irisin; nor has a drug been developed for use in humans. Thus, such agents would have tremendous implications for weight loss.

Thus, there exists a current need for a unique composition including irisin-stimulating ingredients that could activate irisin to promote the "browning" of white adipose tissue so that it behaves like BAT, and/or BAT-activating ingredients, which could in turn increase metabolism and enhance weight loss.

SUMMARY

The present invention includes a method of activating irisin by administering to an individual in need of such treatment a composition comprising irisin-activating ingredients, thus increasing the conversion of white fat to BAT, and consequently, increasing metabolic rate and promoting weight loss. The composition may optionally comprise additional ingredients to activate the increased BAT, thus further increasing metabolic rate and furthering weight loss. The composition can include a *Gynostemma pentaphyllum* extract. The composition can further include a *Polygonum cuspidatum* root extract. The composition can further include capsaicinoids. The composition can further include grains of paradise or constituents thereof.

An objective of the present invention is to offer a method of using a composition comprising irisin-activating ingredients, and optionally additional BAT-activating ingredients, to activate irisin, increase the metabolic rate, and promote weight loss, in the body of a mammal, including a human.

DETAILED DESCRIPTION

Figure 1:
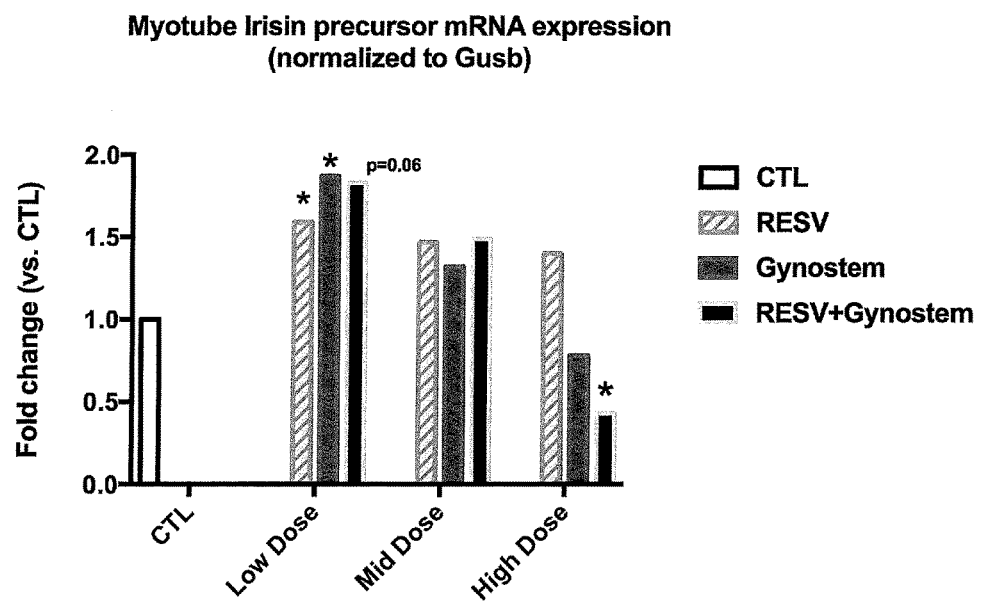
FIG. 1 shows, in an embodiment, irisin gene (mRNA) expression results of a preclinical trial from administration of irisin-stimulating ingredients to a C2C12 muscle cell culture. *p<0.05 statistically significant difference from control. CTL: blank bar. Low, Mid, and High Dose (left to right): RESV, diagonally-striped bar; Gynostem, grey bar; RESV+Gynostem, black bar.

As used herein, the terms "brown adipose tissue (BAT)" and "brown fat" are intended to be generally interchangeable.

As described above, research has demonstrated that brown fat activators, such as capsaicinoids and grains of paradise, are clinically shown to increase metabolism through brown fat oxidation. However, the same research demonstrates that certain individuals did not respond to grains of paradise treatment because they lacked the necessary amount of brown fat to be activated. Brown fat levels in the body can play an important role in body fat regulation. Since the discovery of BAT, scientists have been seeking ways to activate dormant BAT, with little success.

Irisin, discovered in 2012, causes the "browning" of fat, converting inactive white fat into metabolically active BAT. Thus far, no supplement, food, or drug has been developed for use in humans to activate irisin. Such a supplement, food, or drug would be completely novel and have tremendous implications for increasing metabolic rate and promoting weight loss.

Peroxisome proliferator-activated receptor gamma coactivator-1α ("PGC1 alpha" or "PGC-1α") is a critical co-activator protein that activates several transcription factors that increase fat oxidation, metabolism, whole body energy expenditure, and mitochondria biogenesis. PGC1 alpha also lowers oxidative stress and inflammation. Activation of this pathway results in improved fat loss, exercise performance, and metabolism, including improved insulin sensitivity and decreased risk for diseases such as diabetes. PGC1 alpha is also implicated in retarding the aging process. Irisin is activated by PGC1 alpha.

In a series of studies, scientists demonstrated that an increase in irisin and the "browning" of fat was driven and dependent upon activation of the PGC1 alpha signaling pathway. Specifically, exercise increases the expression levels of PGC-1α in the muscle. This, in turn, upregulates the expression of FNDC5, a type I membrane protein, which is C-terminally cleaved and secreted as irisin into circulation. Binding of irisin to receptors on the surface of adipocytes in white fat (white adipose tissue, "WAT") changes their genetic profile. Irisin induces the expression of PPAR-α, which is thought to be an intermediate downstream effector that increases the expression of UCP1. The "browning" of WAT is also associated with augmented mitochondrial density (i.e., increased mitochondria) and oxygen consumption. As discussed above, "browning" is accompanied by an increase in the energy expenditure profile, leading to favorable effects on metabolism. See, e.g., P. Boström et al., supra.

Two primary proteins that regulate PGC1 alpha are AMPK and Sirtuin proteins (i.e., SIRT 1 and SIRT 3).

AMPK (AMP-activated protein kinase) is an intracellular metabolite sensing protein kinase found in all eukaryotes. AMPK is a heterotrimer protein, consisting of α-, β-, and γ-subunits, and exists generally in muscle cells in abundance, and also in the brain, heart, adipose tissue, and liver. AMPK has been proposed as the master cellular "energy sensor" and functions as an important sensor that senses an energy level within cells, and thereby plays an important role in appetite regulation, weight regulation, blood glucose regulation, and blood lipid metabolism regulation. AMPK acts to shut down processes that consume energy (fat-building), and conversely stimulates processes that produce energy (fat-burning and mitochondrial biogenesis).

Many of the metabolic outcomes from exercise are attributed to AMPK activation; thus, AMPK has been dubbed the exercise "switch." When ATP consumption increases AMP concentration by intensive exercise or prolonged starvation, AMP is coupled to the γ-subunit of AMPK, thereby activating AMPK. The activation actually occurs through the phosphorylation of a threonine residue of the α-subunit of AMPK by a super-ordinate phosphorylation enzyme. Phosphorylated AMPK inhibits the synthesis of fatty acid and cholesterol, which is an ATP-consuming biochemical reaction, but activates β-oxidation of fatty acid and glycolysis, which generates ATP. Phosphorylated AMPK phosphorylates a serine residue of acetyl-CoA carboxylase ("ACC"), which is a subordinate protein and a main enzyme for fatty acid synthesis, thereby inhibiting the enzymatic activity of ACC. As a result, AMPK activation reduces the generation of malonyl-CoA, which is a main metabolite for fatty acid synthesis, thereby inhibiting the fatty acid synthesis. The reduction of malonyl-CoA increases the introduction of fatty acids of long chain acetyl-CoA into mitochondria, increasing β-oxidation, thereby reducing body fat.

AMPK activation further causes the phosphorylation of PGC-1α and also activates silent information regulatory T1 ("SIRT1"), which is a kind of histone deacetylase. SIRT1 removes an acetyl group from proteins. PGC-1α is therefore phosphorylated and deacetylated by AMPK and SIRT1, respectively, thereby activating mitochondrial metabolism, and reducing body fat. Because the activation of AMPK inhibits the synthesis of fatty acid and cholesterol in the body, and accelerates the β-oxidation of body fat, it is believed any material capable of activating AMPK can be very effectively used for the enhancement of metabolism and weight loss.

Without being bound by theory, it is further believed that supplements that activate the PGC1 alpha pathway will increase irisin. Two PGC1 alpha agonists include botanical extract from Dolwoe (*Gynostemma pentaphyllum*), standardized to at least 1% saponin, and *Polygonum cuspidatum* root extract (standardized for 50% resveratrol).

*Gynostemma pentaphyllum* is a perennial vine of the family Cucurbitaceae, which grows naturally in forests of mountains or fields. The *Gynostemma pentaphyllum* plant is distantly related to the cucumber. *Gynostemma pentaphyllum* not only activates AMPK, but also shuttles excess fats into the mitochondria to be utilized for energy and safe disposal, which results in efficient energy production and a sharp reduction in unnecessary fat storage. See P. H. Nguyen et al., *New dammarane-type glucosides as potential activators of AMP-activated protein kinase (AMPK) from Gynostemma pentaphyllum*, 19 BIOORGANIC MEDICINAL CHEMISTRY 6254 (2011).

Leaf extracts of *Gynostemma pentaphyllum* have been shown to reduce body weight gain and fat accumulation. In a preclinical study, obese mice supplemented with *Gynostemma pentaphyllum* showed impressive declines in markers associated with obesity and its related diseases. In just eight weeks, *Gynostemma pentaphyllum* supplements resulted in an 8.1% decrease in body weight gain, a 10.3% reduction of deep fat, a 15.5% reduction in abdominal lining fat, an 18.8% reduction in liver weight, and a 14.2% reduction in blood cholesterol. See R. Gauhar et al., *Heat-processed Gynostemma pentaphyllum extract improves obesity in ob/ob mice by activating AMP-activated protein kinase*, 34 BIOTECHNOL. LETT. 1607 (2012). Obese rats supplemented for just four days with *Gynostemma pentaphyllum* extracts demonstrated, compared to controls, 33% reduced triglycerides, 13% reduced total cholesterol, 33% reduced LDL cholesterol, and 20% lower after-meal blood glucose. See S. Megalli et al., *Anti-hyperlipidemic and hypoglycemic effects of Gynostemma pentaphyllum in the Zucker fatty rat*, 9 J. PHARM. PHARM. SCI. 281 (2006). Cell culture experiments with *Gynostemma pentaphyllum* extracts demonstrated more than 2-fold increase in fat burning and a 1.7-fold increase in cellular glucose uptake. See R. Gauhar et al., supra. These results demonstrate the enormous beneficial impact of reducing circulating sugar and fats in response to AMPK activation by *Gynostemma pentaphyllum*.

A human study included overweight and obese people with no active disease who took a placebo or 450 mg daily of a concentrated *Gynostemma pentaphyllum* extract for 12 weeks. The supplemented group showed significant reduction in total abdominal fat area of 3.24 square inches compared to 0.44 square inches for the placebo group, and significant reduction in belly fat area of 1.81 square inches compared to 0.45 square inches for the placebo group. Subjects supplemented with *Gynostemma pentaphyllum* showed a loss of more than an inch in abdominal circumference, and a half-inch in hip circumference. See S. H. Park et al., *Antiobesity effect of Gynostemma pentaphyllum extract (actiponin): a randomized, double-blind, placebo-controlled trial*, 22 OBESITY 63 (2014).

Extracts from the roots of *Polygonum cuspidatum* plants, containing resveratrol, have long been known to be useful in the prevention and therapy of atherosclerosis. See H. Arichi et al., 30 CHEM. PHARM. BULL. 1766 (1982). Resveratrol is a natural polyphenolic flavonoid that is also found in the seeds and skins of grapes, red wine, mulberries, peanuts, and rhubarb. Resveratrol has been shown to increase skeletal muscle mitochondrial biogenesis and fatty acid oxidation in many tissues as well as exercise performance in mice. See V. W. Dolinsky et al., *Improvements in skeletal muscle strength and cardiac function induced by resveratrol during exercise training contribute to enhanced exercise performance in rats*, 590 J. PHYSIOLOGY 2783 (2012). Resveratrol has also been shown to induce AMPK in the skeletal muscle of mice. See J. A. Baur & D. A. Sinclair, *Therapeutic potential of resveratrol: The in vivo evidence*, 5 NATURE REVS. DRUG DISCOVERY 493 (2006); M. Lagouge et al., *Resveratrol improves mitochondrial function and protects against metabolic disease by activating SIRT1 and PGC-1 alpha*, 127 CELL 1109 (2206). However, when SIRT1 was knocked out, these effects were absent. See N. L. Price et al., *SIRT1 is required for AMPK activation and the beneficial effects of resveratrol on mitochondrial function*, 15 CELL METABOLISM 675 (2012).

Resveratrol has been touted for its exercise-mimetic effect through its activation of SIRT1 and AMPK. See N. Hart et al., *Resveratrol enhances exercise training responses in rats selectively bred for high running performance*, 61 FOOD & CHEMICAL TECH. 53 (2013). It has been shown that resveratrol supplementation increases the exercise performance in aged mice and mice fed by a Western diet in the absence of exercise training, suggesting that resveratrol can stimulate pathways similar to exercise. See M. Lagouge et al., supra; T. Murase et al., *Suppression of the aging-associated decline in physical performance by a combination of resveratrol intake and habitual exercise in senescence-accelerated mice*, 10 BIOGERONTOLOGY 423 (2009). Mice treated with resveratrol demonstrated elevations in AMPK activation and PGC-1α expression, along with increases in mitochondria in animals fed a high fat diet. See J. A. Baur & D. A. Sinclair, supra. Additionally, enhanced SIRT1 activity, such as exercise training, decreases plasma glucose levels, improves insulin sensitivity, increases the number and activity of mitochondria, decreases adiposity, improves exercise tolerance, and potentially lowers body weight. See P. J. Elliott & M. Jirousek, *Sirtuins: Novel targets for metabolic disease*, 9 CURR. OPINION IN INVESTIGATIONAL DRUGS 371 (2008). The induction of PGC-1α and activation of AMPK are commonly observed after both exercise and resveratrol administration. See J. A. Baur & D. A. Sinclair, supra; M. Lagouge et al., supra.

In addition to improvement in energy metabolism, resveratrol administration has been correlated with higher aerobic capacity in mice, as shown by increased running time and oxygen consumption in muscle fibers. See K. J. Menzies et al., *Sirtuin 1-mediated effects of exercise and resveratrol on mitochondrial biogenesis*, 288 J. BIOLOGICAL CHEMISTRY 6968 (2013). The findings suggest that resveratrol could be used as a performance enhancer. See J. A. Baur & D. A. Sinclair, supra; M. Lagouge et al., supra. A combination of resveratrol and exercise training has been demonstrated to increase time to exhaustion compared to exercise training alone, as a result of the optimization of fatty acid metabolism by resveratrol, which contributes to increased contractile force response of skeletal muscles. See V. W. Dolinsky et al., supra.

Since the discovery of BAT, scientists have been seeking ways to activate dormant BAT in humans, with little success. No supplement, food, or drug has demonstrated the activation of irisin, which causes the "browning" of fat, or the conversion of inactive WAT into metabolically active BAT. Such a supplement, food, or drug would be completely novel and have tremendous implications for weight loss.

Research has demonstrated that capsaicinoids, and grains of paradise, particularly 6-paradol, are potent brown fat activators. These ingredients are clinically shown to increase metabolism through brown fat oxidation. However, the same research demonstrated that certain individuals did not respond to the grains of paradise treatment and were termed "non-responders." The non-responders were identified to be "BAT negative" people who did not respond because they lacked the necessary amount of brown fat to be activated. Thus, there exists a need for a combination of irisin-stimulating ingredients, which can increase the amount of brown fat in the body, and brown fat activating ingredients, which oxidize brown fat. Such a combination would be completely novel and have tremendous implications for weight loss. There are many forms of capsaicinoids, and many are commercially available. Usually, formulas use a red pepper extract that is standardized to 2% capsaicinoids. In an embodiment, the present invention may contain from about 0.01 mg to about 10 mg of capsaicinoids. In another embodiment, the present invention may contain from about 1 mg to about 100 mg of grains of paradise standardized to 6-paradol.

The dose of *Gynostemma pentaphyllum* extract to be administered in the present invention is from about 1 mg to about 10,000 mg per day in humans, and the dose of *Polygonum cuspidatum* root extract to be administered in the present invention is from about 1 mg to about 10,000 mg per day in humans. In another embodiment, a preferred dose of *Gynostemma pentaphyllum* extract to be administered in the present invention is from about 100 mg to about 500 mg per day in humans, and the dose of *Polygonum cuspidatum* root extract to be administered in the present invention is from about 25 mg to about 500 mg per day in humans. In another embodiment, a more preferred dose of *Gynostemma pentaphyllum* extract to be administered in the present invention is from about 200 mg to about 500 mg per day in humans, and the dose of *Polygonum cuspidatum* root extract to be administered in the present invention is from about 50 mg to about 150 mg per day in humans.

The methods described above may be further understood in connection with the following Examples. In addition, the following non-limiting examples are provided to illustrate the invention.

Example 1

In order to determine if the combination of *Gynostemma pentaphyllum* extract and *Polygonum cuspidatum* root extract would activate the AMPK and SIRT1 pathway, increasing PGC1 alpha signaling, leading to an increase in irisin, a pre-clinical cell culture study in C2C12 cells (muscle tissue) was performed.

Myoblasts were seeded on 6-well plates, and maintained in growth media until 80-90% confluency. Growth media was then removed, and differentiation media was added for 4 days. On day 5, the following 6-hour treatments with serum-free DMEM culture media occurred (n=6 wells per treatment): CTL only (150 µL of EtOH, vehicle); LOW RESV (resveratrol) (10 µM); MID RESV (20 µM); HIGH RESV (50 µM); LOW *Gynostemma pentaphyllum* (60 µg/mL); MID *Gynostemma pentaphyllum* (120 µg/mL); HIGH *Gynostemma pentaphyllum* (240 µg/mL); LOW COMBO (10 µM RESV+60 µg/mL *Gynostemma pentaphyllum*); MID COMBO (20 µM RESV+120 µg/mL ActivAMP); and HIGH COMBO (50 µM RESV+240 µg/mL *Gynostemma pentaphyllum*).

The results were impressive and showed that the combination of *Gynostemma pentaphyllum* extract standardized to at least 1% saponin and *Polygonum cuspidatum* root extract (standardized for 50% resveratrol) increases irisin gene (mRNA) expression by up to 1.83-fold over control, as seen in FIG. 1.

Example 2

In order to determine how myoblasts responded to treatment with the combination of *Gynostemma pentaphyllum* extract and *Polygonum cuspidatum* root extract, the muscle cell culture study was continued by treating myoblasts with resveratrol and *Gynostemma pentaphyllum* over a period of several days. Myoblasts were seeded on 6-well plates and maintained in growth media until 80-90% confluency. Growth media was then removed and differentiation media was added for 4 days. On each of days 5, 6, and 7, 6-hour treatment with serum-free DMEM culture media occurred (n=6 wells per treatment): CTL only (15 µL of EtOH, vehicle); AICAR (1 mM) (AICAR is a potent AMPK stimulator that was used as a positive control); RESV (10 µM); LOW *Gynostemma pentaphyllum* (30 µg/mL); MID *Gynostemma pentaphyllum* (60 µg/mL); LOW COMBO (5 µM RESV+30 µg/mL *Gynostemma pentaphyllum*); and HIGH COMBO (10 µM RESV+60 µg/mL ActivAMP). After the day 7 6-hour treatment, cells were lysed and media was collected at 2 hours post-treatment and 24 hours post-treatment. Statistics were run using a t-tests compared back to the CTL.

Figure 2:
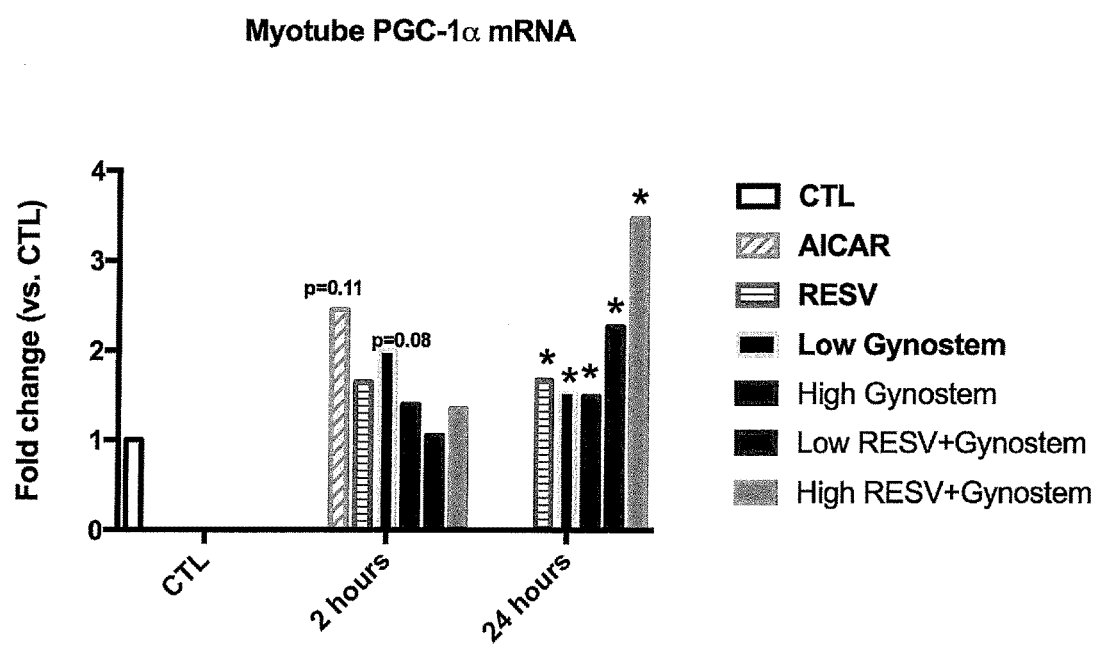
FIG. 2 shows, in an embodiment, myotube PGC-1α mRNA expression results of a preclinical trial from administration of irisin-stimulating ingredients to a C2C12 muscle cell culture. *p<0.05 statistically significant difference from control. CTL: blank bar. 2 hours, 24 hours (left to right): AICAR, diagonally-striped bar; RESV, horizontally-striped bar; Low Gynostem, narrow black bar; High Gynostem, first wide black bar; Low RESV+Gynostem, second wide black bar; High RESV+Gynostem, grey bar.

As seen in FIG. 2, notations * and ** indicate a difference from CTL myotubes ($p<0.05$, $p<0.01$, respectively); almost all treatments increased PGC-1α mRNA 24 hours following the last treatment.

Figure 3:
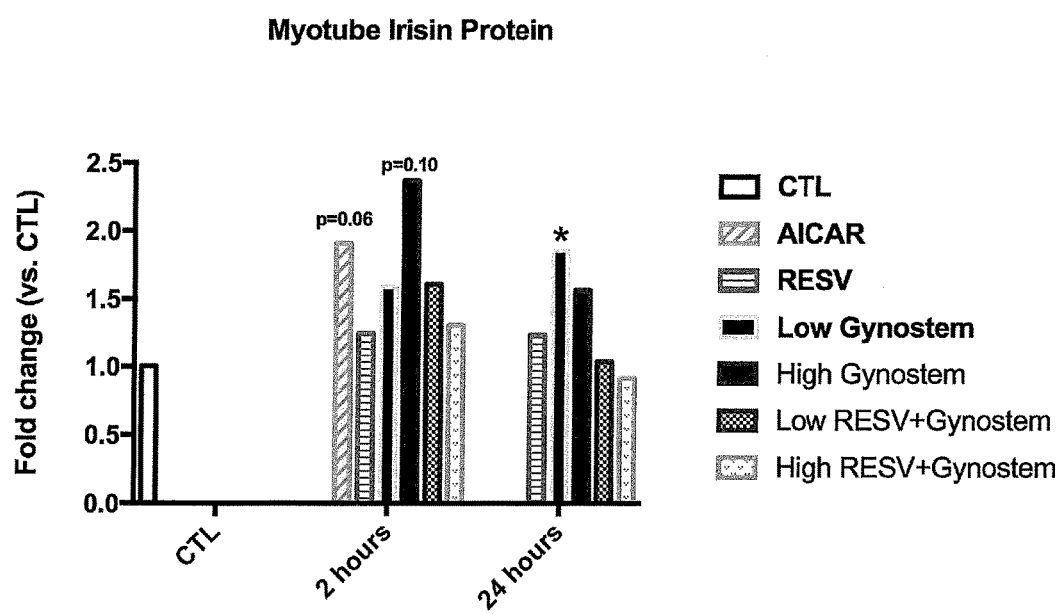
FIG. 3 shows, in an embodiment, irisin protein expression results of a preclinical trial from administration of irisin-stimulating ingredients to a C2C12 muscle cell culture. *p<0.05 statistically significant difference from control. CTL: blank bar. 2 hours, 24 hours (left to right): AICAR, diagonally-striped bar; RESV, horizontally-striped bar; Low Gynostem, narrow black bar; High Gynostem, wide black bar; Low RESV+Gynostem, checkered bar; High RESV+Gynostem, pattern on white bar.

As seen in FIG. 3, notation * indicates a difference from CTL myotubes ($p<0.05$). There was a significant increase of irisin protein expression, and even a doubling of irisin protein expression in the cell cultures that were administered only *Gynostemma pentaphyllum*.

Figure 4:
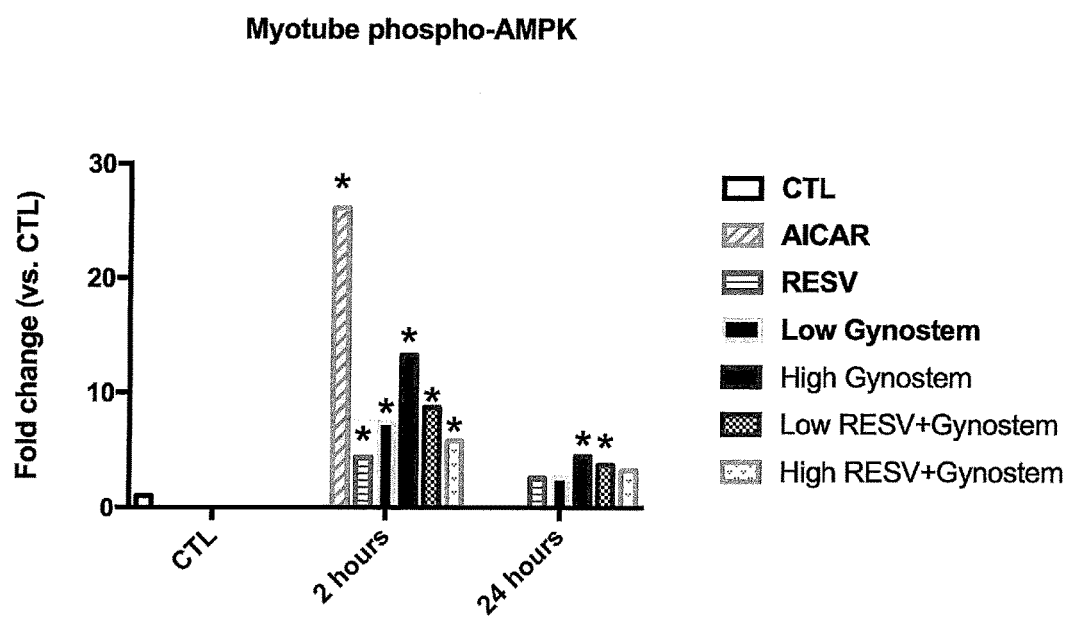
FIG. 4 shows, in an embodiment, phosphorylation (activation) of AMPK results of a preclinical trial from administration of irisin-stimulating ingredients to a C2C12 muscle cell culture. *p<0.05 statistically significant difference from control. CTL: blank bar. 2 hours, 24 hours (left to right): AICAR, diagonally-striped bar; RESV, horizontally-striped bar; Low Gynostem, narrow black bar; High Gynostem, wide black bar; Low RESV+Gynostem, checkered bar; High RESV+Gynostem, pattern on white bar.

As seen in FIG. 4, notations *, , and * indicate a difference from CTL myotubes ($p<0.05$, 0.01, 0.001 respectively). Almost all treatments increased phosphorylation (activation) of AMPK at 2 hours.

Figure 5:
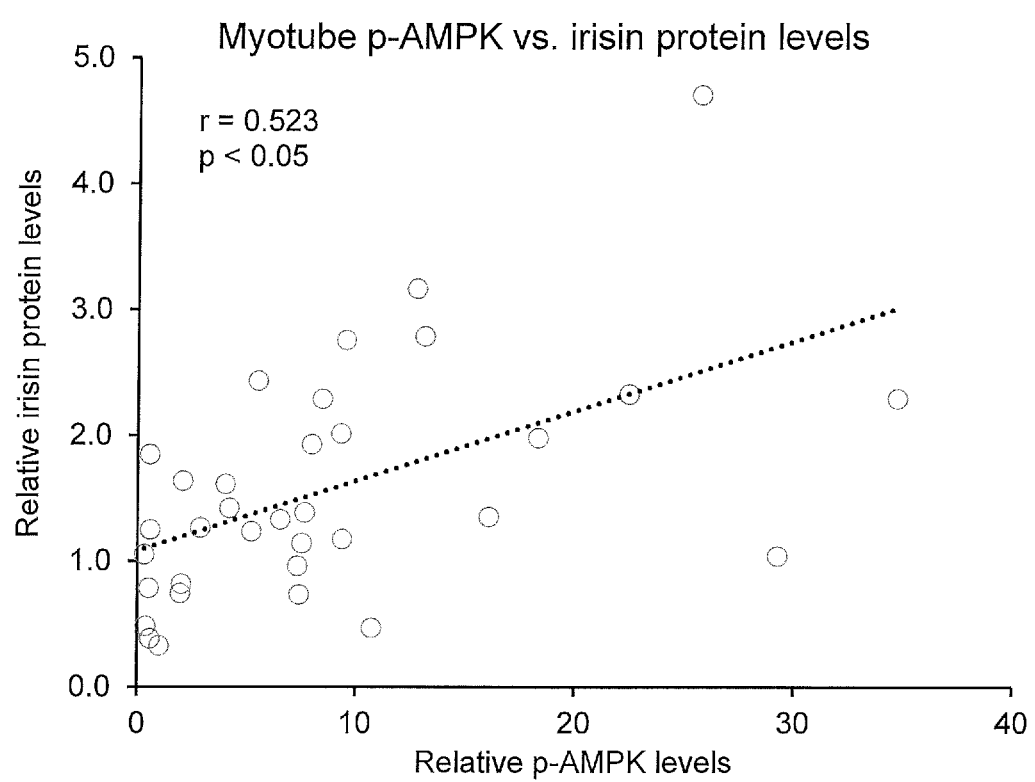
FIG. 5 shows, in an embodiment, the correlation between irisin-stimulating ingredients and irisin protein expression in a C2C12 muscle cell culture. *p<0.05 statistically significant difference from control.

As seen in FIG. 5, consistent with the predicted mechanism action, there was a significant positive correlation between phosphorylation (activation) of AMPK and irisin protein expression in the 2-hour treatments.

Example 3

In order to determine how the combination of *Gynostemma pentaphyllum* extract and *Polygonum cuspidatum* root extract impacted body composition in humans, an embodiment of the present invention, featuring *Gynostemma pentaphyllum* and resveratrol, was created. The embodiment was combined with several additional fat-burning ingredients, including *Aframomum melegueta* seed extract (standardized for 12.5% 6-paradol), which has been shown to increase metabolism through the activation of brown adipose tissue in humans, to create a "Fat Burner Blend." J. Sugita et al., *Grains of paradise (Aframomum melegueta) extract activates brown adipose tissue and increases whole-body energy expenditure in men*, BR. J. NUTR. 1 (2013).

TABLE 1

Fat Burner Blend Formula
Supplement Facts
Serving Size: 2 capsules

|  | Amount Per Serving | % Daily Value |
|---|---|---|
| Vitamin $B_6$ | 10 mg | 500% |
| Chromium | 250 mcg | 208% |
| Fat Burner Blend[a] | 1,102.5 mg | * |

[a]*Gynostemma pentaphyllum* leaf extract from about 200 to about 500 mg; *Polygonum cuspidatum* root extract from about 50 to about 150 mg; *Aframomum melegueta* seed extract (12.5% 6-paradol) from about 1 mg to about 100 mg; cayenne pepper fruit extract; raspberry ketone; caffeine anhydrous; green tea leaf extract; *citrus aurantium* unripe fruit extract; *mucuna pruriens* extract; *Yohimbe* bark extract.
* Daily value not established.

Methods

Over a period of 28 days, male and female subjects (19-35 years old, BMI 23-28) were given one single serving of the fat burner blend comprising an embodiment of the present invention (N=15 "group A" subjects) or a placebo (N=10 "group B" subjects) daily in the morning. The subjects were free living, and told to maintain their normal dietary and exercise habits during the trial. All data was statistically compared using repeated measures ANOVAs and t-tests.

Figure 6:
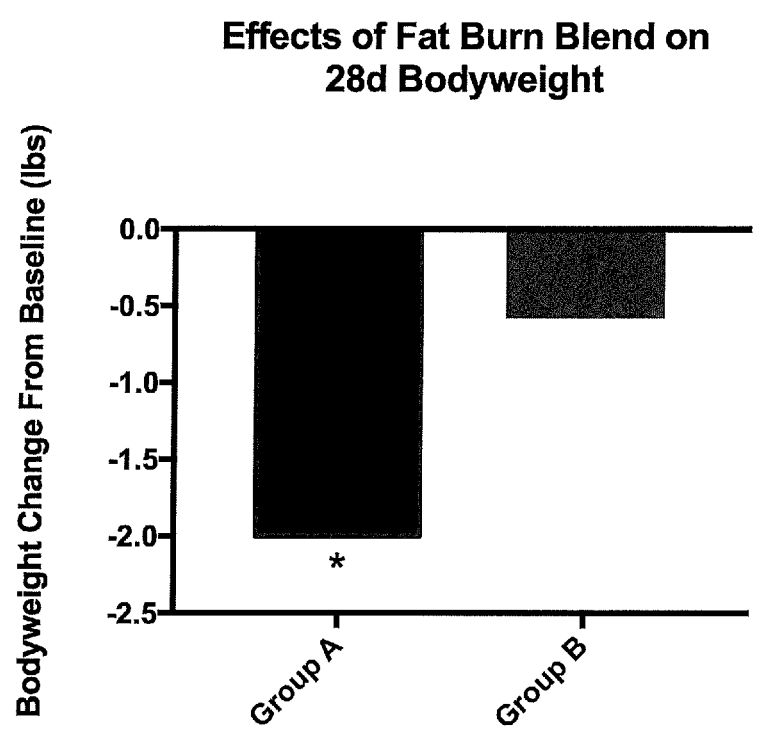
FIG. 6 shows, in an embodiment, body weight data results of subjects in a human clinical trial after 28 days of administration of a composition comprising irisin-stimulating ingredients. *p<0.05 statistically significant difference from control. Group A=treatment group; Group B=placebo.

As seen in FIG. 6, after 28 days of supplementation, the subjects taking the fat burner blend comprising an embodiment of the present invention significantly lost 2.0 lbs of body weight. DEXA analysis of body composition also showed that there was a statistically significant loss in body fat with the fat burner blend comprising an embodiment of the present invention, suggesting preferential fat loss. There was no statistically significant reduction in body weight or body fat for the placebo group.

Figure 7:
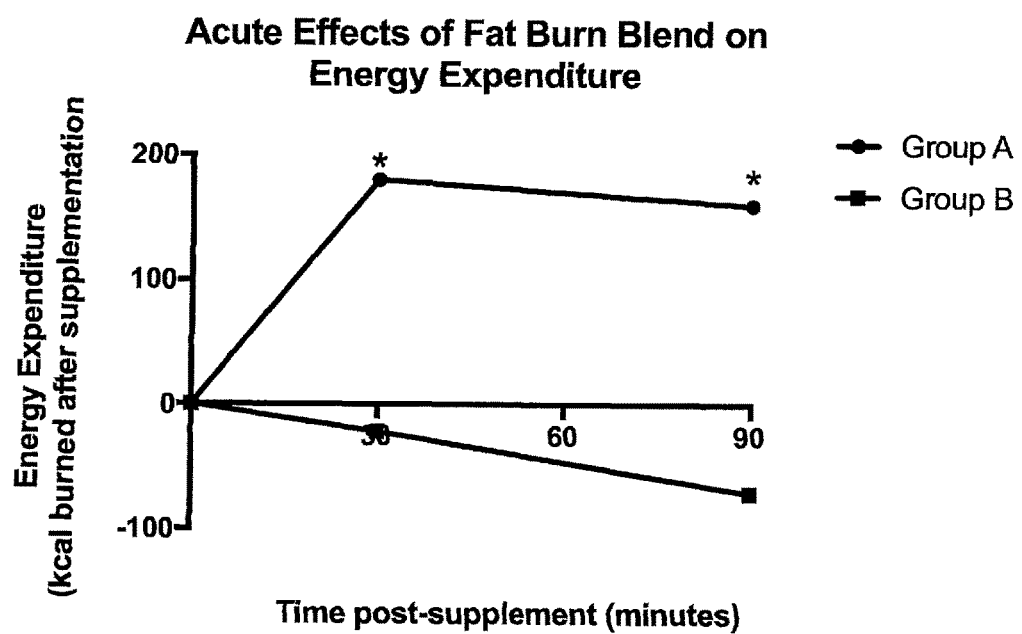
FIG. 7 shows, in an embodiment, energy expenditure data results of subjects in a human clinical trial after 28 days of administration of a composition comprising irisin-stimulating ingredients. *p<0.05 statistically significant difference from control. Group A=treatment group; Group B=placebo.

As seen in FIG. 7, on day 28, subjects came into the lab having fasted, and energy expenditure at 30 and 90 minutes immediately after supplementation was measured. It was found that the fat burner blend comprising an embodiment of the present invention significantly increased metabolism at 30 and 90 minute time-points, which approximated over 230 kilocalories higher than placebo control at 90 minutes.

In a satisfaction questionnaire 11/15 (73%) of subjects were satisfied with supplement A; 2/10 (20%) of subjects were satisfied with supplement B.

Thus in its principal embodiment the present invention offers a combination, and method of use thereof, of *Gynostemma pentaphyllum* extract and *Polygonum cuspidatum* root extract optionally with brown fat activating ingredients that contain capsaicinoids and/or grains of paradise (standardized for 6-paradol) to induce the body of a mammal, for example a human, to enhance irisin expression, increasing the amount of brown fat, consequently enhancing metabolic rate and weight loss. It is believed that the administration of the formulations as described herein will afford unexpected advantages and potentially synergistic effects, etc.

The product(s) of the present invention may be formulated into nutraceutical or pharmaceutical dosage forms comprising of tablets, capsules, powders, liquids, chews, gummies, transdermals, injectables, etc. using standard excipients and formulation techniques in the industry. The product of the subject invention may be administered to the mammal orally in solid dosage form or by parenteral or transdermal administration.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof and, accordingly, reference should be made to the appended claims, rather than to the foregoing specification, as indicating the scope of the invention.

The invention claimed is:

1. A method of increasing irisin levels in the body of a human, comprising administering to a human in need of weight loss a composition comprising about 200 mg to about 500 mg of a *Gynostemma pentaphyllum* extract, about 1 mg to about 100 mg of grains of paradise, and about 50 mg to about 150 mg of a *Polygonum cuspidatum* root extract, wherein the human has a body mass index ("BMI") from about 23 to about 28, and wherein the metabolic rate of the human increased at least 200 kilocalories within 90 minutes after administration following daily administration of the composition for 28 days.

2. The method of claim 1, wherein the amount of brown adipose tissue in a human is increased.

3. The method of claim 1, wherein the body weight of a human is decreased.

4. The method of claim 3, wherein the body weight of a human is decreased by at least 1.5 lbs following daily administration of the composition for 28 days.

5. The method of claim 1, wherein the composition further comprises from about 0.01 mg to about 10 mg of capsaicinoids.

6. The method of claim 5, wherein the amount of brown adipose tissue in a human is increased.

7. The method of claim 5, wherein the body weight of a human is decreased.

8. The method of claim 7, wherein the body weight of a human is decreased by at least 1.5 lbs following daily administration of the composition for 28 days.

* * * * *